(12) United States Patent
Pfeiffer et al.

(10) Patent No.: US 6,631,286 B2
(45) Date of Patent: Oct. 7, 2003

(54) DEVICE FOR THE DETERMINATION OF TISSUE PERFUSION AND OPERATIVE USE THEREOF

(75) Inventors: Ulrich J. Pfeiffer, Munich (DE); Andreas Becker, Markt Schwaben (DE); Norbert Eder, Winhoring (DE); Thorsten Burger, Munich (DE); Christian Töns, Moers (DE)

(73) Assignee: Pulsion Medical Systems AG, Munich (DE)

( * ) Notice: Subject to any disclaimer, the term of this patent is extended or adjusted under 35 U.S.C. 154(b) by 20 days.

(21) Appl. No.: 09/993,901

(22) Filed: Nov. 27, 2001

(65) Prior Publication Data

US 2002/0099279 A1 Jul. 25, 2002

(30) Foreign Application Priority Data

Nov. 28, 2000 (DE) .......................... 100 59 070

(51) Int. Cl.⁷ .................................. A61B 6/00
(52) U.S. Cl. .................... 600/473; 600/476; 424/9.6
(58) Field of Search .................... 600/473, 476; 424/9.6

(56) References Cited

U.S. PATENT DOCUMENTS

| 5,074,306 A | 12/1991 | Green et al. |
| 5,363,854 A | 11/1994 | Martens et al. |
| 5,400,791 A | 3/1995 | Schlier et al. |
| 5,813,987 A | * 9/1998 | Modell et al. |
| 6,032,070 A | 2/2000 | Flock et al. |
| 6,081,612 A | 6/2000 | Gutkowicz-Krusin et al. |

OTHER PUBLICATIONS

Joseph Still et al., "Evaluation of the Circulation of Reconstructive Flaps Using Laser–Induced Fluorescence of Indocyanine Green", Annals of Plastic Surgery, 1999, vol. 42, pp. 266–274.
Jeffery S. Reynolds et al. Imaging of Spontaneous Canine Mammary Tumors Using Fluorescent Contrast Agents, Photochemistry and Photobiology, 1999, 70(1), pp. 87–94.
Albert Rubben et al., "Infrared Videoangiofluorography of the Skin with Indocyanine Green–Rat Random Cutaneous Flap Model and Results in Man", Microvascular Research, 1994, vol. 47, pp. 240–251.
Patent Abstracts of Japan Publication No. 10–201707, "Endoscope Apparatus" Publication Date: Aug. 4, 1999 Inventor: Nakamura Kazunari.
Still et al., "Evaluation of the Circulation of Reconstructive Flaps Using Laser–Induced Fluorescence of Indocyanine Green", pp. 266–274, Mar. 1999, Annals of Plastic Surgery, vol. 42, No. 3.
European Search Report, Dated Mar. 26, 2002.

* cited by examiner

Primary Examiner—Marvin M. Lateef
Assistant Examiner—Barry Pass
(74) Attorney, Agent, or Firm—Nixon Peabody LLP; Donald R. Studebaker

(57) ABSTRACT

A safety housing, into which an infrared laser light source is integrated together with the CCD camera, forms a compact unit for the determination of tissue perfusion. Rays from the infrared laser light source radiate the area of operation and indocyanin green, previously injected intravenously into the patient, is excited to fluorescence by the radiation, which is detected by the CCD camera.

25 Claims, 2 Drawing Sheets

DEVICE FOR THE DETERMINATION OF TISSUE PERFUSION AND OPERATIVE USE THEREOF

BACKGROUND OF THE INVENTION

The present invention relates to a device for the determination of tissue perfusion in applications in which the wearing of safety glasses would constitute a hindrance, and the operative use of such a device.

A device and process for angiofluorography of the skin are described in "Microvascular Research" 1994, Vol. 47, pp. 240–251. In this case, after application of indocynanin green, the blood circulation through the skin is assessed on the basis of the fluorescence signal, which occurs as a result of excitation by means of radiation in the near-infrared range. There serves as radiation source here a 2000 watt halogen lamp with a bandpass filter connected in front of it as well as a water filter necessary because of high heat development. A CCD camera serves as detector.

A device and process for examining burns by means of fluorescence measurements after application of an exogenous chromophore are disclosed in U.S. Pat. No. 5,074,306. The imaging apparatus consists of a xenon or mercury vapour lamp as excitation light source, an intensified CCD camera and a computer with image processing software.

If halogen or mercury vapour lamps are used as light sources for excitation of the chromophore, then these must have a relatively high power, as only a short wavelength range of the broad-band radiation is usable for fluorescence excitation, and the rest of the generated light must be filtered out by means of a bandpass filter. The necessary high lamp power in the kilowatt range results in correspondingly high heat generation, which requires cooling measures, and also in a large structure in particular of the electrical components. Portable, mains-independent configurations are therefore not possible with such light sources.

A device and process for measuring the blood circulation through transferred skin grafts, wherein after application of indocyanin green the fluorescence excited by radiation with a pulsed laser array is detected with a CCD camera, are known from "Annals of Plastic Surgery" 1999, Vol. 42, pp. 266–274.

A device and process for tumour detection in animal tissue, wherein after application of indocyanin green the fluorescence excited by radiation with a pulsed laser diode is detected with a CCD camera, are described in "Photochemistry and Photobiology" 1999, 70(1), pp. 87–94.

The use of appropriate laser light sources requires safety glasses to be worn when handling the systems and also requires that the rooms in which they are applied are identified for safety reasons. This is not a significant problem for purely diagnostic tasks, but renders such systems unsuitable for operative application, since special laser protection measures would have a disruptive effect in routine surgical use.

A device for infrared video angiography of the fundus of the eye, which has a near-infrared light source for the excitation of fluorescence of indocyanin green as well as a detector camera, is disclosed in U.S. Pat. No. 5,400,791.

However, the device disclosed in U.S. Pat. No. 5,400,791 is not suitable for operative observation of a larger operating area because of its design for ophthalmological diagnostics.

SUMMARY OF THE INVENTION

In view of the poor suitability of conventional diagnostic devices based on the fluorescence excitation of a chromophore for routine application in the operating theatre, the object forming the basis of the present invention is to provide a device for the operative determination of tissue perfusion, which is easy to handle, is also suitable for non-microinvasive procedures and in particular renders special protective measures such as the wearing of safety glasses superfluous.

Accordingly the present invention provides a device for the determination of tissue perfusion in applications in which the wearing of safety glasses would constitute a hindrance, said device including:

a radiation source, said source generating an electromagnetic bundle of rays in a wavelength range corresponding to the wavelength range of the fluorescence excitation of a chromophore;

an optical expansion unit;

a safety housing; and an electronic camera with an optical filter, said filter being transparent to emitted light of the excited chromophore and opaque to the wavelength range of said generated bundle of rays;

wherein said radiation source and said optical expansion unit are integrated into said safety housing whereby only an expanded bundle of rays with an intensity not exceeding a limit value that excludes any risk to persons present in the vicinity of the device, can emerge from said safety housing, and said optical expansion unit enables the illumination of an operating area sufficiently large for non-microinvasive procedures.

The present invention also provides a method of using the above device for the determination of tissue perfusion, wherein the determination occurs operatively, i.e. during a surgical operation.

BRIEF DESCRIPTION OF THE DRAWINGS

A preferred embodiment of the present invention will now be described, by way of example only, with reference to the accompanying drawings which are not to scale, wherein.

DESCRIPTION OF THE PREFERRED EMBODIMENT

Figure 1:
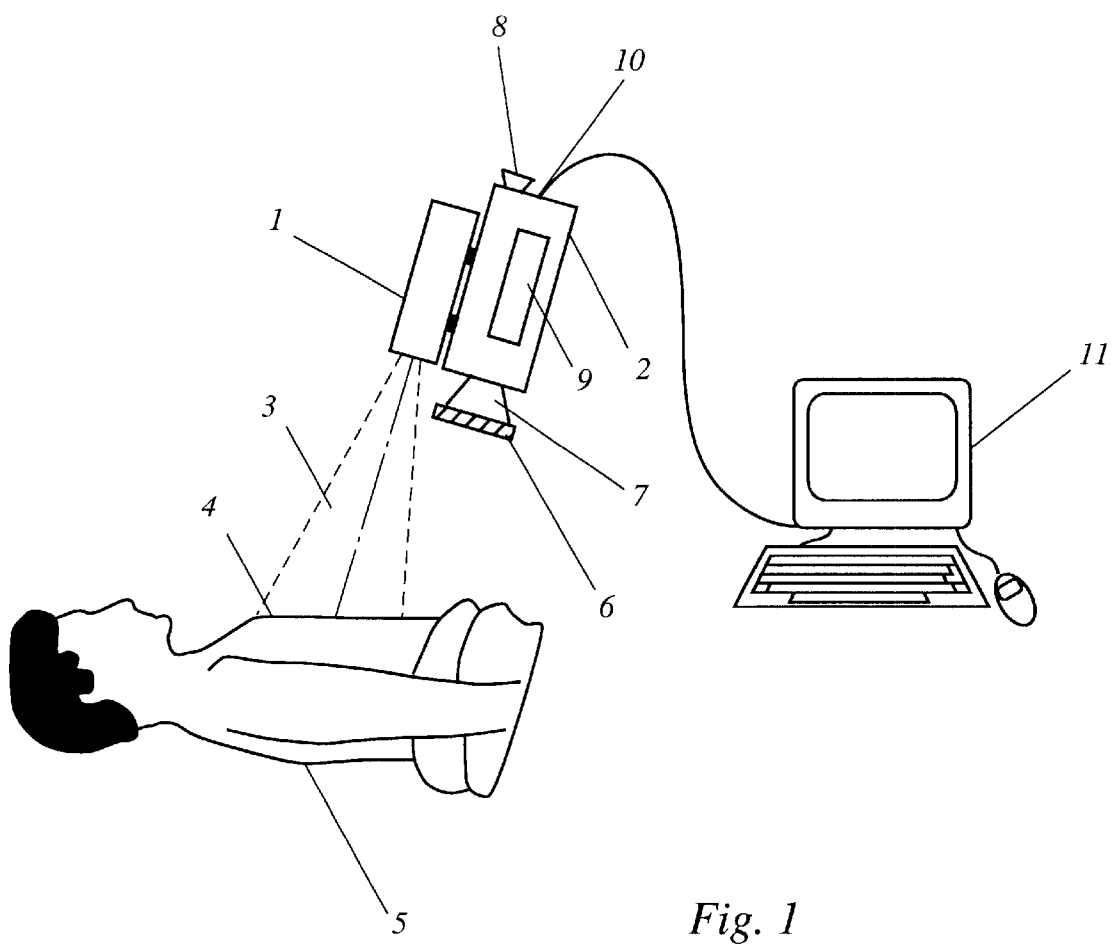
FIG. 1 shows the schematic arrangement of a device according to the invention during operative application.

Basically, the invention provides a device for the determination of tissue perfusion, which has a radiation source, which generates a bundle of rays in a wavelength range corresponding to the wavelength range of the fluorescence excitation of a chromophore, and has an optical expansion unit as well as a safety housing and an electronic camera with an optical filter, which is transparent to emitted light of the excited chromophore and opaque to the wavelength of the generated laser beam. In this case, the radiation source and the optical expansion unit are integrated into the safety housing such that only an expanded bundle of rays with an intensity, which does not exceed a limit value that excludes any risk to persons present in the vicinity of the device, can emerge from the safety housing, and the optical expansion unit enables the illumination of an operating area which is also sufficiently large for non-microinvasive procedures. Thus, the invention is suitable for use in particular in cases where the quantification of the blood circulation through tissue during a procedure can be decisive, i.e. in the area of visceral surgery in left-side colectomies and proctectomies, in gastric transposition after oesophagectomy, in free transplants of the small intestine for interposition as well as all Roux-Y reconstructions (after gastrectomy, as biliodigestive anastomoses etc.). The device is also suitable for the detection of secondary perfusion disorders in the case of strangulated hernia or bridenileus. In heart surgery the device can be used to examine the efficiency of coronary bypasses. In the field of plastic surgery, it is possible to check the perfusion of transferred grafts as well as assess the tissue damage in the case of traumas (e.g. navicular fractures, comminuted fractures, soft-tissue injuries and also gunshot injuries).

Preferably, said radiation source is a light-emitting diode unit with bundled emission or an infrared laser light source.

The limit value that excludes any risk to persons present in the vicinity of the device without safety glasses can preferably be taken from the European Standard EN 60825-1. For the near-infrared range, the maximum permissible radiation (MPR) for the action of laser radiation on the cornea of the eye with exposure times in the order of magnitude relevant for the medical application of the present invention is calculated here according to the formula MPR= $18 \cdot t^{0.75} \cdot C_4 \cdot C_6$ $J \cdot m^{-2}$, wherein t relates to the exposure time and the parameters $C_4$ and $C_6$ result as follows: for a peak wavelength $\lambda$ of the infrared laser light source between 700 and 1050 nm $C_4 = 10^{0.002 \cdot ((\lambda/nm - 700))}$. If the angular expansion $\alpha$ of the apparent source (i.e. of the expanded laser beam upon emergence from the safety housing), measured at a distance of at least 100 mm from the eye of the observer, is greater than $\alpha_{max} = 100$ mrad and the exposure time is greater than or equal to 10 seconds, then $C_6 = \alpha_{max}/\alpha_{min} = 100$ mrad/11 mrad=9.09 (where $\alpha_{min} = 11$ mrad). It follows that, with an exposure time of more than 10 seconds, the limit value that excludes any risk to persons present in the vicinity of the device for the intensity of the expanded laser beam emerging from the safety housing must be less than the term $9.2 \cdot 10^{0.002 \cdot ((\lambda/nm - 700))}$ $mW \cdot cm^{-2}$, as a result of which the limit value for the preferred field of application lies below about 13.4 $mW/cm^2$.

In a preferred embodiment, the infrared laser light source has at least one laser diode; particularly suitable is a number from 1 to 10 diodes, the power of which lies in the range from below 1 mW to 1 W, preferably between below 1 W and 300 mW.

Advantageously, the infrared laser light source may also be pulsed or modulated.

The optical expansion unit preferably has at least one diffusing lens and at least one collecting lens.

Advantageously, an element of the optical expansion unit, preferably one of the lenses, is frosted.

The divergence of the expanded bundle of rays emerging from the safety housing preferably amounts to between 0° and 40°.

In order to cover a sufficiently large surface, the optical expansion unit enables the radiation of a preferably 10 to 40 cm wide area at a distance of preferably 20 to 200 cm from the safety housing.

Indocyanin green is preferably used as chromophore. In this case, an infrared laser light source with a peak emission in the wavelength range between 750 nm and 810 nm, preferably 780 nm, is suitable for excitation.

In a particularly advantageous further development, the device has an accumulator and can therefore be operated independently of the mains. The absence of a mains cable prevents any potential restrictions in the freedom of movement of the surgeon and other participants in a procedure.

In a particularly preferred embodiment, the electronic camera, which may be a standard commercially available CCD video camera, may be carried and operated with one hand.

In an advantageous further development, the safety housing and the electronic camera are combined to form a compact unit.

In an advantageous embodiment, the device has an interface, preferably for digital image transmission, in which case image transmission may also be achieved without cables.

In a further advantageous embodiment, the device can be remote-controlled, and is mounted, for example, on the ceiling above the operating table. As a result, it may be operated by one person, who is not participating directly in the surgical operation, so that any disruption to the progress of the operation as a result of the measurement is minimal.

The camera preferably has a viewfinder or an integrated LCD screen, thus rendering unnecessary an external display screen, whose space requirement and necessary cable connection to the camera could restrict the freedom of movement of the surgeon and other participants in the procedure.

The device is preferably equipped with a storage means, e.g. in the form of a memory chip or a video cassette, so that image data may be recorded.

In an advantageous further development of the invention, the device has an electronic image evaluation system.

Referring now to the drawings, FIG. 1 shows the arrangement of a device according to the invention during operative application schematically and not to scale. The safety housing 1, into which the infrared laser light source with a peak emission of 780 nm is integrated, together with the CCD camera 2, forms a compact unit which may be carried and operated with one hand, is equipped with an accumulator and can therefore be used independently of the mains.

The expanded laser light 3 emerging from the safety housing 1 has a surface-related intensity of below 1 $mW/cm^2$, and therefore lies below the limit value of the maximum permissible radiation of the cornea of the eye (MPR), as a result of which no safety glasses have to be worn in the area surrounding the device.

The expanded bundle of rays 3 of the infrared laser light source radiates the approximately 30 cm wide area of operation 4, which is located at a distance of approximately 70 cm from the safety housing 1. Indocyanin previously injected intravenously into the patient 5 as a bolus in a dosage of between 0.1 and 2 mg per kg of body weight is excited to fluorescence by the radiation.

The fluorescence signal is detected by the CCD camera 2, which is sensitive in the near-infrared wavelength range, a filter 6 being connected in front of said camera. The filter 6 is an NIR long-wave pass filter (cut-off filter), which is only transparent to wavelengths greater than 800 nm and is screwed to the autofocus lens of the CCD camera 2 by means of an external thread. Alternatively, a filter, which permits narrow-band transmission in the range of the fluorescence maximum of the chromophore indocyanin green, is also suitable. The CCD camera 2 has a viewfinder 8, so that no external monitor needs to be used during the operation, and therefore a cable connection which may disrupt handling is unnecessary. The electronic image data of the detected fluorescence are recorded digitally on a video cassette 9.

A sterile cloth (not shown) may be disposed between the patient 5 and the unit comprising CCD camera 2 and safety housing 1, so that the device itself does not need to be sterile. However, because of the compact design and the absence of cable connections, the unit comprising CCD camera 2 and safety housing 1 can also be easily packed in a sterile manner.

An electronic image processing and evaluation system 11 can be connected via an interface 10 in accordance with IEEE 1394, which permits a data transfer rate of up to 400 MBit/s, to the CCD camera 2, which enables the brightness of the individual image elements (pixels) to be taken quantitatively as measure of the intensity of fluorescence. For this, various image regions (regions of interest) can be marked by the user on the first image of an image sequence to then determine the brightness of the pixels in this region image by image and display the results graphically. In this case, a region of tissue to be examined can be directly compared with a reference region with normal perfusion or with an external standard (e.g. fluorescence foil) of known intensity. It is also possible to compare image sequences, which have been received with different radiation and detector parameters, directly with one another when using an external standard. By evaluation of the entire image sequence it is possible to apply various criteria to the evaluation, e.g. the rate of ebb and flow of the chromophore and the change in intensity of fluorescence caused by the chromophore in the tissue regions.

Figure 2:
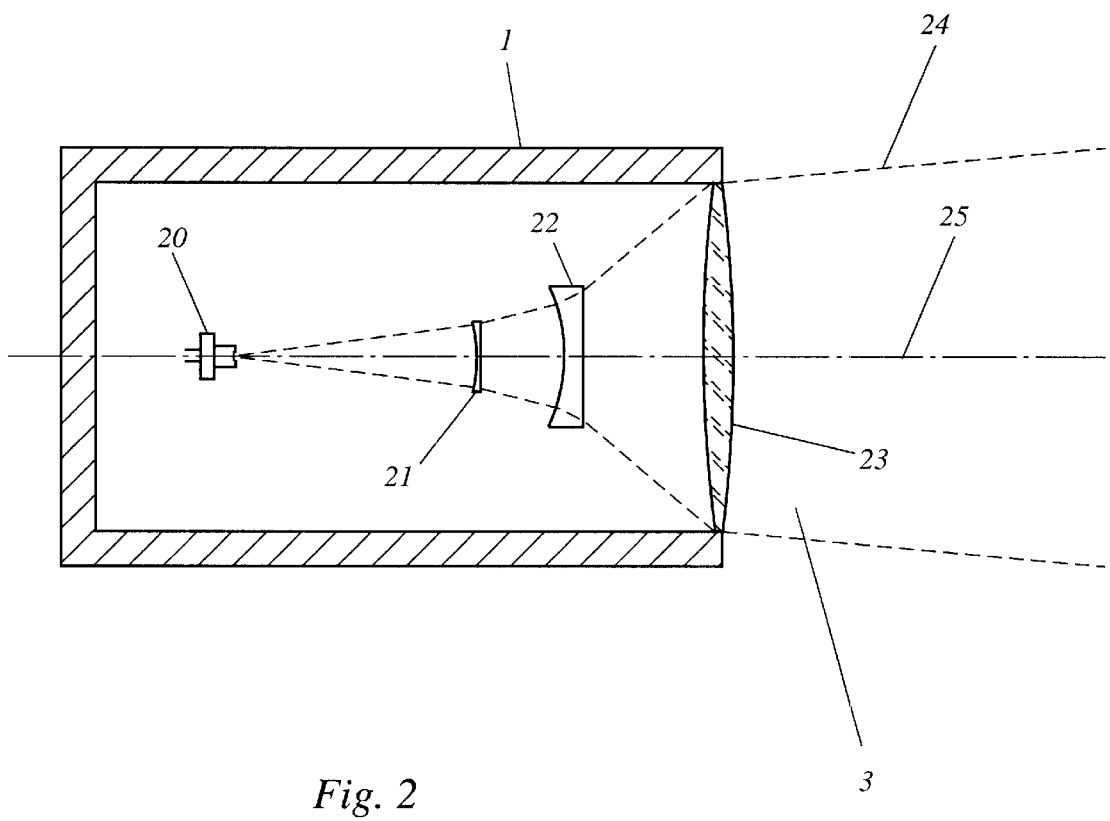
FIG. 2 shows the schematic structure of the safety housing of the device of FIG. 1 with integrated laser diode and optical beam expansion unit.

FIG. 2 schematically shows the structure of the safety housing 1 of the device of FIG. 1 with integrated laser diode 20 and optical beam expansion unit, which comprises the diffusing lens 21 and 22 and the frosted collecting lens 23. The bundle of rays 3 emerging from the safety housing has a divergence of 10° (corresponding to an angle of 5° between the marginal ray 24 and the optical axis 25). The optical expansion unit ensures that no radiation emerges from the safety housing 1 which poses a risk to persons present in the vicinity of the device without special additional protective measures, such as wearing safety glasses, having to be taken for this.

It will be understood that the above description of the present invention is susceptible to various modifications, changes and adaptations.

What is claimed is:

1. A device for the determination of tissue perfusion in applications in which the wearing of safety glasses would constitute a hindrance, said device including:
   a radiation source, said source generating an electromagnetic bundle of rays in a wavelength range corresponding to the wavelength range of the fluorescence excitation of a chromophore;
   an optical expansion unit;
   a safety housing; and
   an electronic camera with an optical filter, said filter being transparent to emitted light of the excited chromophore and opaque to the wavelength range of said generated bundle of rays;
   wherein said radiation source and said optical expansion unit are integrated into said safety housing adapted to allow only an expanded bundle of rays with an intensity not exceeding a limit value that excludes any risk to persons present in the vicinity of the device, to emerge from said safety housing, and said optical expansion unit enables the illumination of an operating area sufficiently large for non-microinvasive procedures.

2. A device according to claim 1, wherein said radiation source is a light-emitting diode unit with bundled emission.

3. A device according to claim 1, wherein said radiation source is an infrared laser light source.

4. A device according to claim 3, wherein said limit value that excludes any risk to persons present in the vicinity of the device is less than the expression $9.2 \cdot 10^{0.002 \cdot ((\lambda/nm - 700))}$ mW·cm$^{-2}$, wherein $\lambda$ designates the peak wavelength of the infrared laser light source.

5. A device according to claim 3, wherein said limit value that excludes any risk to persons present in the vicinity of the device is less than or equal to 13.4 mW/cm$^2$.

6. A device according to claim 3, wherein said infrared laser light source comprises at least one laser diode.

7. A device according to claim 3, wherein said infrared laser light source is pulsed.

8. A device according to claim 3, wherein said infrared laser light source is modulated.

9. A device according to claim 1, wherein said optical expansion unit comprises at least one diffusing lens and at least one collecting lens.

10. A device according to claim 1, wherein said optical expansion unit has a matt element.

11. A device according to claim 10, wherein said matt element is a frosted lens.

12. A device according to claim 1, wherein said bundle of rays emerging from said safety housing has a divergence of 0° to 40°.

13. A device according to claim 1, wherein said optical expansion unit enables the radiation to be of a 10 to 40 cm wide area at a distance of 20 to 200 cm from said safety housing.

14. A device according to claim 1, wherein said chromophore is indocyanin green.

15. A device according to claim 1 including an accumulator, whereby said device can be operated independently of the mains.

16. A device according to claim 1, wherein said electronic camera can be carried and operated with one hand.

17. A device according to claim 1, wherein said safety housing and the electronic camera are combined to form a compact unit.

18. A device according to claim 1 including an interface for image transmission.

19. A device according to claim 18, wherein said interface for image transmission is an interface for digital image transmission.

20. A device according to claim 1, wherein said device can be remote-controlled.

21. A device according to claim 1, wherein said camera has a viewfinder.

22. A device according to claim 1 including an integrated LCD screen.

23. A device according to claim 1 including at least one storage means for storing image data.

24. A device according to claim 1 including, an electronic image evaluation system.

25. Use of a device according to claim 1 for the determination of tissue perfusion, wherein determination occurs operatively.

* * * * *